United States Patent
Kowaleski

(10) Patent No.: US 7,663,009 B2
(45) Date of Patent: Feb. 16, 2010

(54) PROCESS FOR THE MANUFACTURE OF AN ALKENYL AROMATIC COMPOUND UNDER LOW STEAM-TO-OIL PROCESS CONDITIONS

(75) Inventor: Ruth Mary Kowaleski, Cypress, TX (US)

(73) Assignee: Shell Oil Company, Houston, TX (US)

( * ) Notice: Subject to any disclaimer, the term of this patent is extended or adjusted under 35 U.S.C. 154(b) by 512 days.

(21) Appl. No.: 11/274,990

(22) Filed: Nov. 16, 2005

(65) Prior Publication Data

US 2006/0106267 A1 May 18, 2006

Related U.S. Application Data

(60) Provisional application No. 60/629,266, filed on Nov. 18, 2004.

(51) Int. Cl.
*C07C 2/76* (2006.01)
(52) U.S. Cl. .................. 585/444; 585/440
(58) Field of Classification Search ............ 585/444, 585/440
See application file for complete search history.

(56) References Cited

U.S. PATENT DOCUMENTS

| | | | |
|---|---|---|---|
| 1,327,061 A | 1/1920 | Penniman | |
| 1,368,748 A | 2/1921 | Penniman et al. | |
| 2,127,907 A | 8/1938 | Fireman | 23/200 |
| 2,990,432 A | 6/1961 | Fleming et al. | 260/669 |
| 3,900,525 A | 8/1975 | Christmann et al. | 260/680 E |
| 3,904,552 A | 9/1975 | O'Hara | 252/458 |
| 4,150,063 A | 4/1979 | Besozzi et al. | 260/680 E |
| 4,229,603 A | 10/1980 | Lyon | 585/444 |
| 4,978,789 A | 12/1990 | Taniguchi et al. | 564/305 |
| 5,023,225 A | 6/1991 | Williams et al. | 502/304 |
| 5,032,180 A | 7/1991 | Krockert et al. | 106/459 |
| 5,190,906 A | 3/1993 | Murakami et al. | 502/304 |
| 5,614,012 A | 3/1997 | Pitzer | 106/456 |
| 5,668,075 A | 9/1997 | Milam et al. | 502/338 |
| 5,689,023 A | 11/1997 | Hamilton, Jr. | 585/444 |
| 5,689,203 A | 11/1997 | Geist | 327/187 |
| 5,911,967 A | 6/1999 | Ruthner | 423/632 |
| 5,962,757 A | 10/1999 | Milam et al. | 585/444 |
| 6,100,436 A * | 8/2000 | Wiede et al. | 585/440 |
| 6,117,228 A | 9/2000 | Burow et al. | 106/456 |
| 6,184,174 B1 | 2/2001 | Rubini et al. | 502/304 |
| 6,231,661 B1 | 5/2001 | Hayashi et al. | 106/456 |
| 6,465,704 B2 | 10/2002 | Williams et al. | 585/444 |
| 2001/0020118 A1 | 9/2001 | Williams et al. | 585/444 |
| 2003/0144566 A1 | 7/2003 | Culp et al. | 585/444 |
| 2003/0223942 A1 | 12/2003 | Lister et al. | 424/63 |
| 2006/0106267 A1 | 5/2006 | Kowaleski | 585/444 |

FOREIGN PATENT DOCUMENTS

| | | |
|---|---|---|
| EP | 0181999 A1 | 6/1985 |
| EP | 0502510 | 3/1992 |
| EP | 0894528 | 7/1998 |
| EP | 1388523 A2 | 7/2003 |
| WO | 99/49968 | 3/1999 |

OTHER PUBLICATIONS

International Search Report for PCT/US2005/041685 of Mar. 28, 2006.

* cited by examiner

*Primary Examiner*—Thuan Dinh Dang

(57) ABSTRACT

An improved dehydrogenation process that comprises the dehydrogenation of dehydrogenatable hydrocarbons by the utilization of an iron oxide based dehydrogenation catalyst composition having a low titanium content under low steam-to-oil process conditions.

4 Claims, 4 Drawing Sheets

Figure 1:
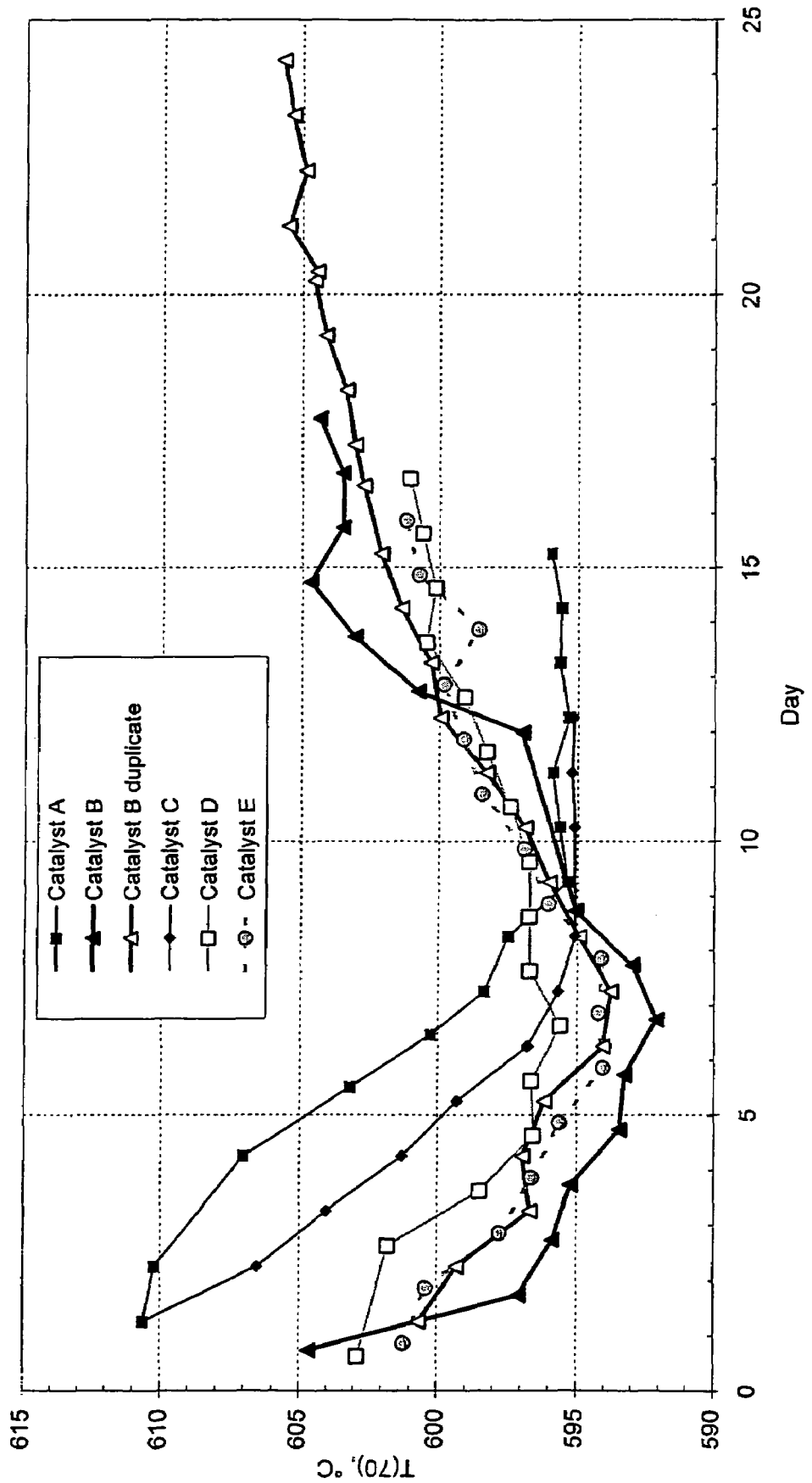

PROCESS FOR THE MANUFACTURE OF AN ALKENYL AROMATIC COMPOUND UNDER LOW STEAM-TO-OIL PROCESS CONDITIONS

This application claims the benefit of U.S. Provisional Application No. 60/629,266 filed Nov. 18, 2004, the entire disclosure of which is hereby incorporated by reference.

The invention relates to an improved process for the manufacture of an alkenyl aromatic compound which process uses, under low steam-to-oil operating conditions, a dehydrogenation catalyst having a low titanium content.

The dehydrogenation of alkyl aromatic compounds is conventionally carried out on a commercial scale by passing an alkyl aromatic containing feed at an elevated temperature through a reaction zone containing a dehydrogenation catalyst. Steam is typically mixed with the alkyl aromatic feed prior to its introduction into and contacting with the dehydrogenation catalyst of the reaction zone. The steam may serve as both a diluent and a heat source. As a heat source, the steam raises the temperature of the alkyl aromatic feed to a dehydrogenation temperature, and it supplies the endothermic heat energy required by the resulting dehydrogenation reaction. As a diluent, the presence of a steam atmosphere in the reaction zone during the dehydrogenation reaction inhibits the formation and deposition on the dehydrogenation catalyst of carbonaceous residues, and it otherwise prolongs the useful life of the dehydrogenation catalyst. Typically, the stability and, thus, the useful life, of the dehydrogenation catalyst are improved with the use of higher steam-to-oil ratios.

It is desirable from an energy savings standpoint to be able to operate a dehydrogenation process at as low of a steam-to-oil ratio as is possible. But, as suggested above, the operation of a dehydrogenation process at a reduced steam-to-oil ratio tends to cause the dehydrogenation catalyst to deactivate at an unacceptable rate thereby making the operation at such low steam-to-oil ratio commercially impractical. There have, however, been ongoing efforts to improve the operation and energy efficiency of dehydrogenation processes either through the development of various catalysts that exhibit good catalytic properties such as high stability when used with feeds having low steam-to-oil ratios or through the development of other methods that allow for the use of a low steam-to-oil ratio.

One example of the effort is presented in U.S. Pat. No. 4,064,187, which discloses a dehydrogenation catalyst that allegedly permits the operation of commercial steam dehydrogenation units at lower steam to hydrocarbon ratios than were previously thought to be practical. The iron oxide ($Fe_2O_3$) containing catalyst taught by this patent is alleged to make possible steam to hydrocarbon feed weight ratios of as low as 0.5:1 (approximate molar ratio of 2.94:1) when used for dehydrogenation of ethylbenzene to styrene and still provide for commercially acceptable conversions and yield but with good catalyst life. The taught catalyst contains major portions of $Fe_2O_3$ and ZnO and lesser amounts of alkali metal chromate and a basic potassium promoter.

In another example, an iron oxide-containing dehydrogenation catalyst is disclosed in U.S. Pat. No. 6,184,174 that allegedly exhibits high activity and selectivity in the dehydrogenation of ethylbenzene to styrene when used under low steam-to-oil feed process conditions. The iron oxide-containing catalyst of the '174 patent contains potassium ferrate in the form of crystallites with numerical average size of less than 2 microns. There is no indication of the stability characteristics of the catalyst of the '174 patent when used under low steam-to-oil process conditions.

U.S. Pat. No. 4,229,603 discloses a method for achieving improved yields in the dehydrogenation of alkyl aromatic compounds under low steam-to-oil process conditions. This method includes introducing an alkyl aromatic feed into a catalyst bed of a reactor, and, thereafter, contacting and mixing the alkyl aromatic feed with steam within the catalyst bed. The steam is introduced into the catalyst bed through a tube that is in heat exchange relationship with the catalyst of the catalyst bed and the reaction gases of the dehydrogenation reaction. The '603 patent discloses an apparatus and methodology for lowering the steam-to-oil ratio in a dehydrogenation process, but this lowering of the steam-to-oil ratio does necessarily depend on the use of a particular type of catalyst.

U.S. Pat. No. 5,190,906 teaches the addition of titanium oxide to an iron oxide based dehydrogenation catalyst for the purpose of enhancing the catalytic performance of the catalyst. The '906 patent asserts that the addition of from 0.005 to 0.95 wt. % (50 ppmw to 9500 ppmw) titanium oxide to the mixture of catalytic components of an iron oxide based dehydrogenation catalyst improves the performance of the catalyst, but the patent fails to recognize that the presence of titanium in an iron oxide based dehydrogenation catalyst provides a catalyst that with respect to certain performance factors exhibits poorer catalytic performance in low steam-to-oil environments.

As noted above, there have been ongoing efforts by those skilled in the art to develop improved dehydrogenation processes that use reduced ratios of steam-to-oil in their feeds. One of the difficulties, however, with the reduction of the steam-to-oil ratio of a dehydrogenation process feed is that most of the dehydrogenation catalysts available for use in these processes are not commercially effective under such low steam-to-oil conditions. While some of the available dehydrogenation catalysts may exhibit good initial activity and selectivity under low steam-to-oil process conditions, their catalytic performance is not stable because their activity tends to rapidly decline when the catalyst is used under such low steam-to-oil conditions. And, with some catalysts, their activity or selectivity, or both, may even be lower when used under low steam-to-oil process conditions as compared to when they are used under high steam-to-oil process conditions. What is desired is the development of a dehydrogenation process that can be operated at low steam-to-oil process conditions permitted by the use of a catalyst that exhibits good stability characteristics as well as good activity and selectivity characteristics when used under low steam-to-oil process conditions.

It, thus, is an objective of the invention to provide an improved dehydrogenation process that may acceptably be operated under low steam-to-oil process conditions.

Accordingly, the invention provides a dehydrogenation process which includes contacting under dehydrogenation conditions a feed comprising ethylbenzene and steam, wherein the steam is present in the feed in an amount so as to provide a molar steam-to-oil ratio in the feed of less than 9:1, with an iron oxide based dehydrogenation catalyst having a low titanium content. Further, the invention may include a process for the manufacture of styrene, which the process is of the type wherein an ethylbenzene feed is contacted under dehydrogenation conditions with a catalyst to yield a styrene product. The process utilizes as its catalyst an iron oxide based dehydrogenation catalyst composition having low titanium content, and it is operated under low steam-to-oil operating conditions.

Another invention provides a method of improving the operation of a styrene process unit including a reactor containing a first catalyst having a high titanium content, wherein the method comprises removing the first catalyst from the reactor and replacing therewith a second catalyst having a low titanium content; and, thereafter, operating the styrene process unit at a low steam-to-oil ratio process condition.

In yet another invention, a dehydrogenation catalyst is provided that may suitably be used in the dehydrogenation of ethylbenzene to make styrene under a low steam-to-oil ratio process condition. The dehydrogenation catalyst comprises an iron oxide component; a cerium component; a potassium component; a molybdenum component; an alkaline earth metal component; and titanium present in the dehydrogenation catalyst composition at a titanium concentration of less than 1000 ppmw.

FIG. 1 presents plots comparing the dehydrogenation activity (i.e., T(70)) as a function of time at a 10:1 molar ratio of steam-to-hydrocarbon process conditions for iron oxide base dehydrogenation catalysts having differing titanium concentrations with some having high and others having low titanium contents.

Figure 2:
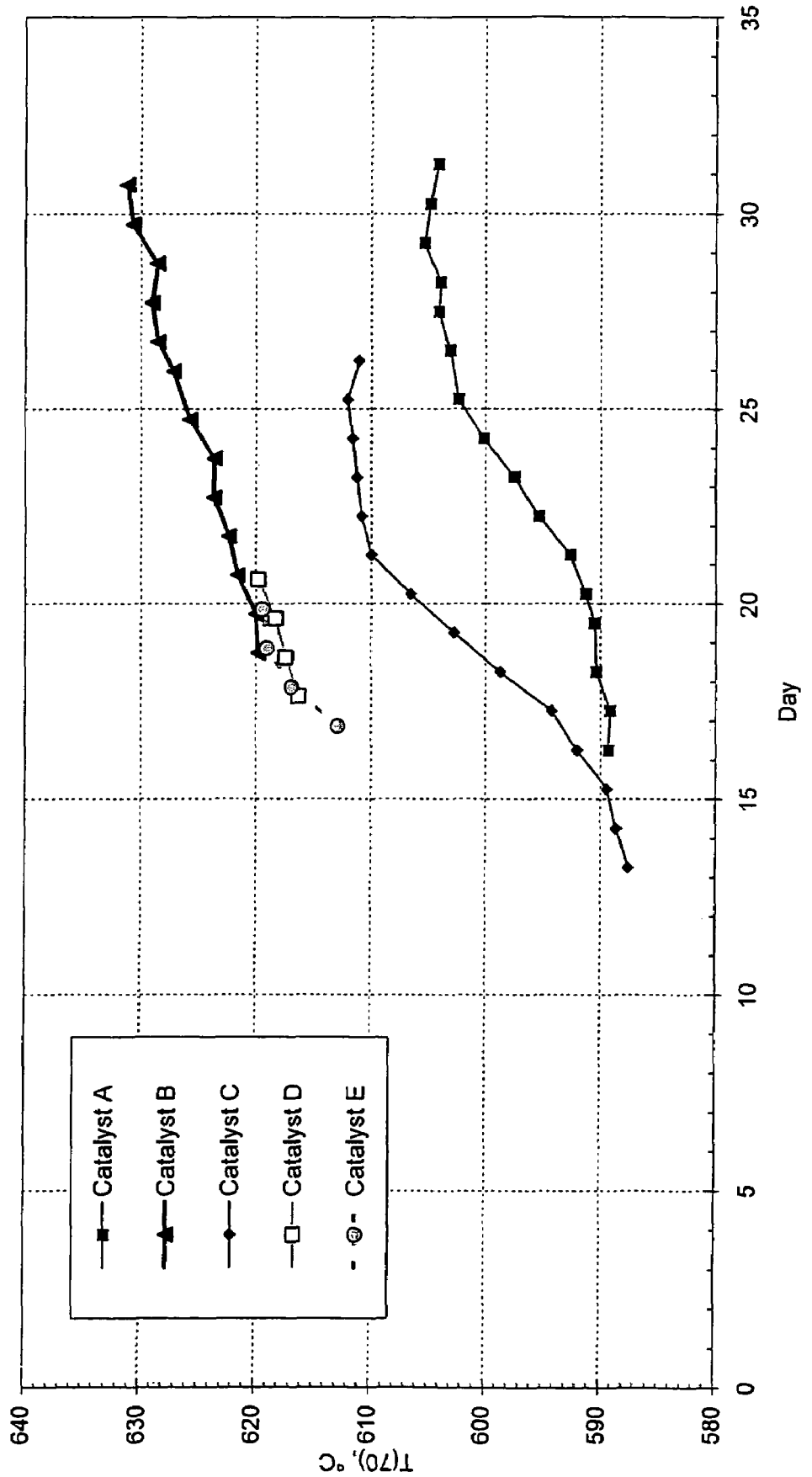

FIG. 2 presents plots comparing the dehydrogenation activity as a function of time for the same catalysts as are presented in FIG. 1; except, that, the steam-to-hydrocarbon molar ratio was 5:1.

Figure 3:
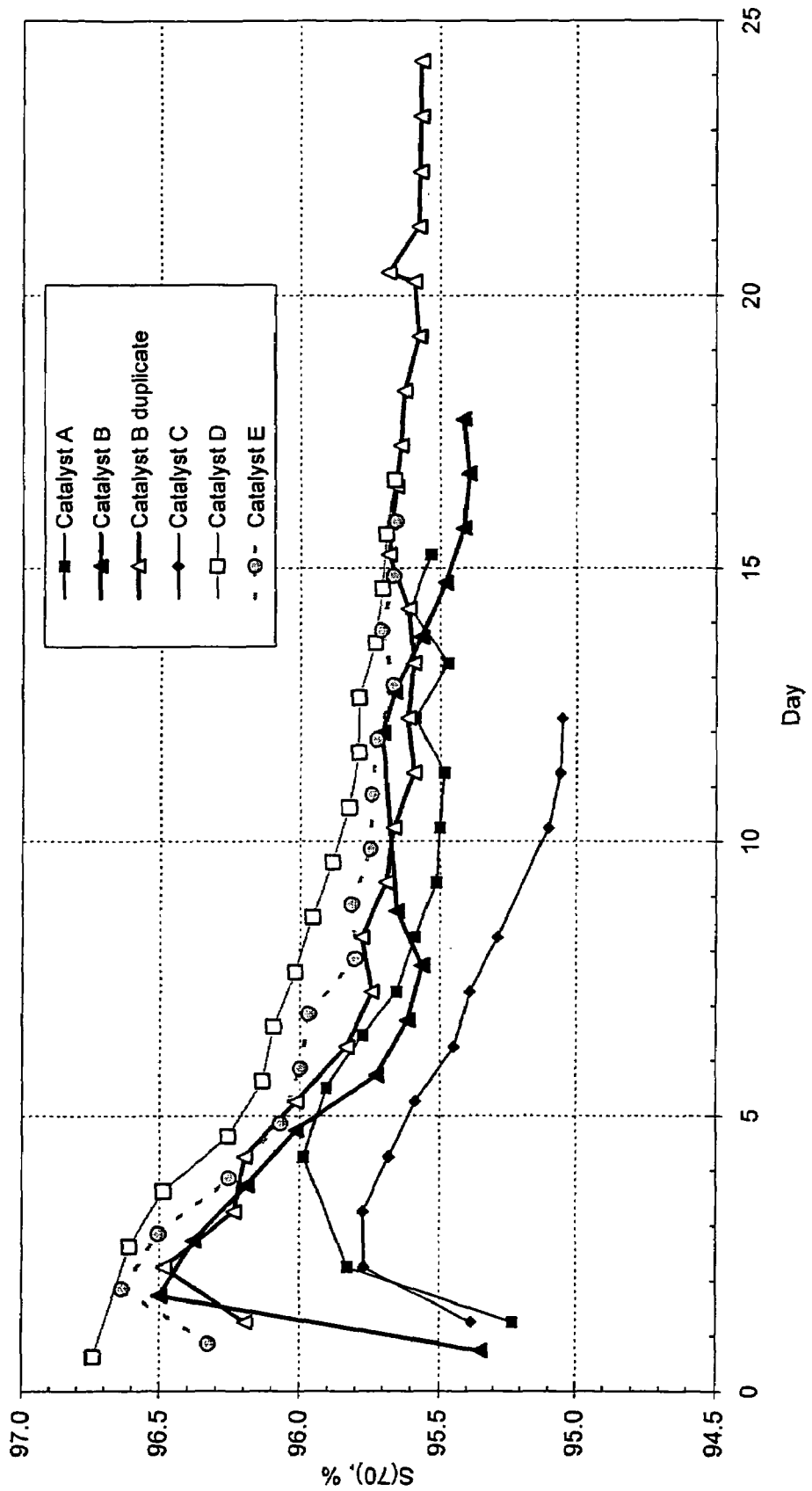

FIG. 3 presents plots comparing the selectivity (i.e., S(70)) as a function of time for the same catalysts and under the same 10:1 molar ratio of steam-to-hydrocarbon process conditions as are presented in FIG. 1.

Figure 4:
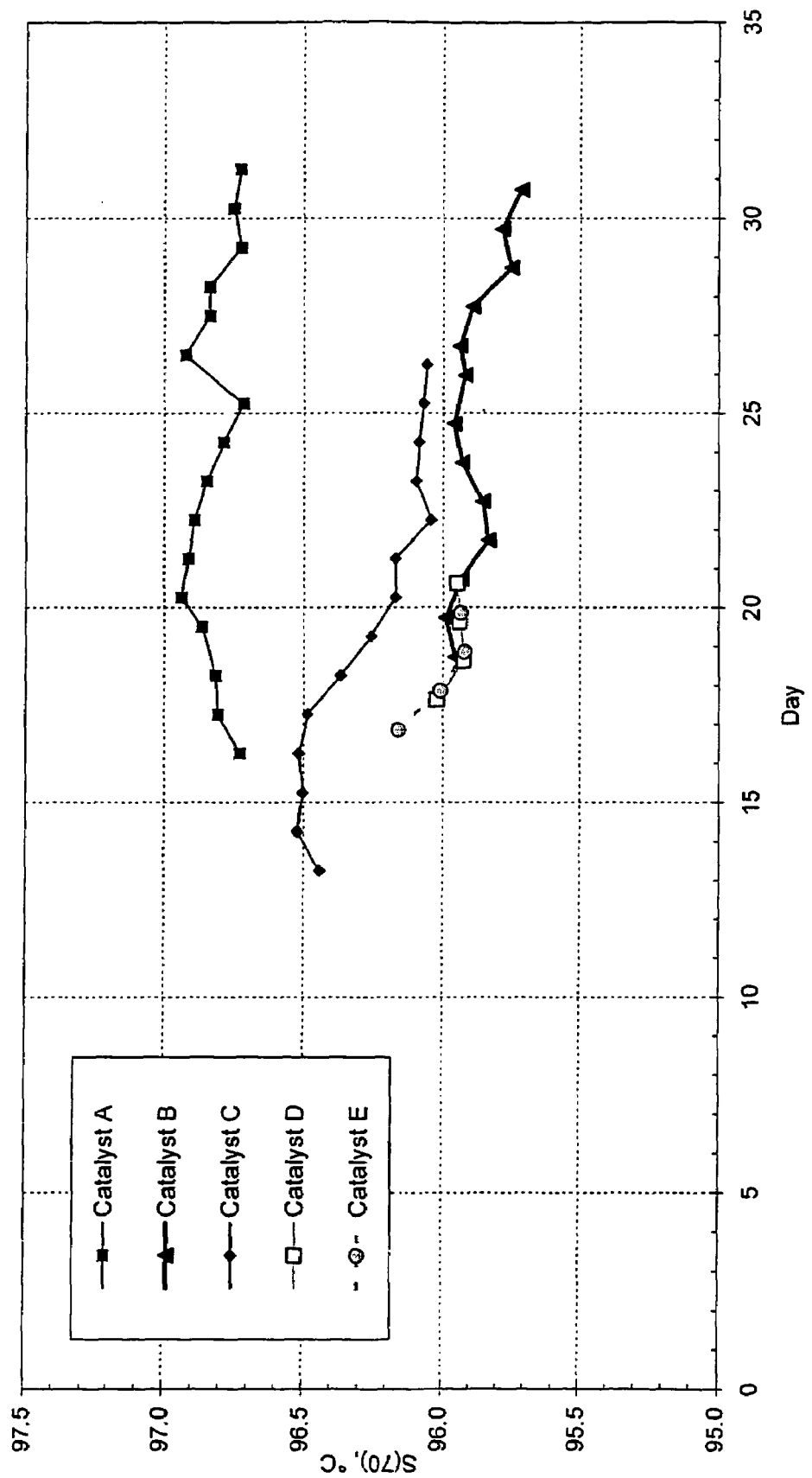

FIG. 4 presents plots comparing the selectivity as a function of time for the same catalysts as are presented in FIG. 1; except, that, the steam-to-hydrocarbon molar ratio was 5:1.

It has been discovered that a process for the catalytic dehydrogenation of an alkyl aromatic compound to an alkenyl aromatic hydrocarbon can be greatly improved by the utilization of an iron oxide based dehydrogenation catalyst composition that has a low titanium content which permits operation of the catalytic dehydrogenation process at low steam-to-oil process conditions with improvements in catalytic activity and selectivity but without unacceptable reductions in catalyst stability or useful life.

The operation of a catalytic dehydrogenation process under low steam-to-oil process conditions can be desirable for a variety of reasons. But, the degree to which the steam-to-oil ratio may be reduced is typically limited by certain of the properties of the dehydrogenation catalyst used in the dehydrogenation process. In general, with the current economic considerations and commercially available dehydrogenation catalysts, the typical operation of a dehydrogenation process utilizes a steam-to-oil ratio exceeding 9:1, and, in most instances, the steam-to-oil ratio used is in the range exceeding 10:1. Many types of commercially available dehydrogenation catalysts even require the utilization of steam-to-oil ratios in the range exceeding 12:1 upwardly to 20:1.

When referring herein to the steam-to-oil ratio or to steam-to-oil process condition or the like, what is meant is that, in a dehydrogenation process in which a feedstock is charged to a dehydrogenation reactor that defines a dehydrogenation reaction zone containing a dehydrogenation catalyst, the value for the steam-to-oil ratio is as determined by dividing the moles of steam in the feedstock by the moles of hydrocarbon in the feedstock. For the case in which the hydrocarbon and steam are not commingled in the feedstock prior to the introduction thereof into the dehydrogenation reactor, the value of the steam-to-oil ratio is that as determined by taking the ratio of the total moles of steam introduced into the dehydrogenation reactor per total moles of hydrocarbon introduced into the dehydrogenation reactor.

The inventive process is an improved method of manufacturing an alkenyl aromatic, such as styrene, by the dehydrogenation of an alkyl aromatic, such as ethylbenzene, involving the operation of a dehydrogenation process at a lower steam-to-oil process condition than is typical. The utilization of an iron oxide based dehydrogenation catalyst that has a low titanium content allows for the stable operation of the dehydrogenation process that is operated under low steam-to-oil process conditions. Also, such a low titanium content dehydrogenation catalyst provides for higher activity and selectivity when used under low steam-to-oil process conditions.

U.S. Pat. No. 5,190,906 teaches that the addition of titanium to an iron oxide dehydrogenation catalyst provides for an enhancement in activity, selectivity and stability of the catalyst. However, the inventive process as described herein exploits the properties of an iron oxide based dehydrogenation catalyst that contains a small amount of titanium, or other words has a small titanium concentration, that permit the operation of the dehydrogenation process at low steam-to-oil process conditions. Also, it is unexpected that the iron oxide based dehydrogenation catalyst having a low titanium concentration exhibits a higher activity and selectivity when used under a low steam-to-oil process condition than the activity and selectivity exhibited by comparable iron oxide catalysts having a high titanium concentration when used under similar low steam-to-oil dehydrogenation process conditions.

When referring herein to the steam-to-oil ratio or process condition as being low, what is meant is that the steam-to-oil ratio, as defined above, that is used in the inventive improved dehydrogenation process is lower than what is used in many conventional dehydrogenation processes. Generally, a low steam-to-oil ratio used in the inventive improved dehydrogenation process is less than 9:1, but, preferably, the low steam-to-oil ratio is less than 8:1. More preferably, the low steam-to-oil ratio is less than 6:1 and even less than 5:1.

Even when using the low titanium content iron oxide dehydrogenation catalyst there can be practical limitations on how low the steam-to-oil ratio may be reduced in the operation of the inventive improved dehydrogenation process; especially, since, much of the endothermic energy for the dehydrogenation reaction is supplied by the steam. But, generally, the lower limit is no lower than 0.1:1 or 0.5:1 or even 1:1. Thus, for example, the low steam-to-oil ratio under which the inventive improved dehydrogenation process is operated can be in the range of from 0.1:1 to 9:1, preferably, in the range of from 0.5:1 to 8:1, and, most preferably, from 1:1 to 6:1, or even from 1:1 to 5:1.

The composition of the dehydrogenation catalyst used in the inventive dehydrogenation process is particularly important to providing for the operational improvements over the prior art dehydrogenation processes. The dehydrogenation catalyst should exhibit catalytic properties that allow for the improvement in the operation of a dehydrogenation process unit, which includes a dehydrogenation reactor containing a first dehydrogenation catalyst, by the removal from the dehydrogenation reactor of the dehydrogenation process unit of the first dehydrogenation catalyst and replacing therewith a second dehydrogenation catalyst. The second dehydrogenation catalyst exhibits such properties as to permit the acceptable commercial operation of the dehydrogenation reactor, which contains the second dehydrogenation catalyst, at low steam-to-oil process conditions. It has been found that an iron oxide based dehydrogenation catalyst composition that is characterized as having low titanium content allows for the low steam-to-oil operation of the dehydrogenation process unit. Iron oxide dehydrogenation catalysts having a high titanium concentration, on the other hand, do not exhibit the properties necessary for allowing the acceptable operation of a dehydrogenation process unit at low steam-to-oil process conditions.

Thus, the catalyst of the inventive processes herein is an iron oxide based dehydrogenation catalyst containing a sufficiently low titanium content so as to allow for the operation of the dehydrogenation process, in which it is used, under low steam-to-oil process conditions. Such a low titanium concentration can be less than about 1000 parts per million by weight (ppmw). But, generally speaking, it is desirable for the titanium content of the iron oxide based dehydrogenation catalyst to be significantly lower and in the range of less than 500 ppmw or even less than 300 ppmw. Preferably, the concentration of titanium in the iron oxide based dehydrogenation catalyst used in the inventive processes herein is in the range of less than 100 ppmw, and, most preferably, less than 75 ppmw.

There is no particular lower limit for the concentration range of titanium in the iron oxide based dehydrogenation catalyst except those limitations due to practical considerations. Thus, the lower limit for the titanium concentration range in the iron oxide based dehydrogenation catalyst of the inventive processes can be at levels of trace quantities, for example, at as low as 1 part per billion by weight (ppbw), and, more particularly, 1 ppmw.

The references herein to the concentration of titanium or titanium content refer to the titanium in the elemental form even though the titanium is probably present in the iron oxide based dehydrogenation catalyst in some other form, such as, as an oxide. Also, the references to concentration measurements in parts by weight are based on the total weight of the iron oxide based dehydrogenation catalyst.

The iron oxide based dehydrogenation catalyst of the inventive process, which has a low titanium concentration, also comprises iron oxide. It further may contain other catalytic components, such as, for example, potassium and at least one additional promoter metal. The potassium and additional promoter metal or metals are assumed to be present in the iron oxide based dehydrogenation catalyst in the oxide form.

The iron oxide of the iron oxide based dehydrogenation catalyst may be in a variety of forms including any one or more of the iron oxides, such as, for example yellow iron oxide (goethite, FeOOH), black iron oxide (magnetite, $Fe_3O_4$), red iron oxide (hematite, $Fe_2O_3$), including synthetic hematite or regenerator iron oxide, restructured iron oxide, and any combination of the aforementioned iron oxides. The iron oxide may also be combined with potassium oxide to form one or more of the phases containing both iron oxide and potassium oxide to form one or more of the phases containing both iron and potassium as represented by the formula $(K_2O)_x \cdot (Fe_2O_3)_y$.

The restructured iron oxide that may be used as a component or in the preparation of the dehydrogenation catalyst of the inventive process is of the type as described in detail in U.S. Pat. No. 5,668,075, which is incorporated herein by reference. As is noted in the '075 patent, the use of restructured iron oxide in the preparation of certain dehydrogenation catalysts can provide for enhanced selectivity. Also, the catalysts prepared by the methods taught by the '075 patent may be used as the dehydrogenation catalyst of the inventive process; provided, that, such catalysts have the necessary low titanium content as noted elsewhere in this specification.

The regenerator iron oxide that may be used as a component or in the preparation of the dehydrogenation catalyst of the inventive process is an iron oxide produced by the spray roasting of an iron chloride solution. Examples of suitable methods by which the regenerator iron oxide is prepared are described in U.S. Pat. No. 5,911,967, which is incorporated herein by reference.

Other types of iron oxide may also be used as a component of or in the preparation of the dehydrogenation catalysts of the inventive process, and they include, for example, Penniman iron oxide made by any of the Penniman or modified Penniman methods such as those taught by such patents as U.S. Pat. No. 1,327,061; U.S. Pat. No. 1,368,748; U.S. Pat. No. 2,127,907; and U.S. Pat. No. 5,032,180, all of which are incorporated herein by reference. An example of a catalyst that may be suitable for use in the inventive process is that as described in U.S. Pat. No. 5,689,023, which discloses the preferred use of large particle iron oxide formulated from iron oxide derived from scrap iron via dehydration of yellow α-FeOOH intermediate, or, in other words, iron oxide derived from yellow iron oxide prepared by the Penniman method. U.S. Pat. No. 5,689,023 is incorporated herein by reference.

Another example of a dehydrogenation catalyst that may be used in the inventive process is an iron oxide based dehydrogenation catalyst that is obtained by combining an iron oxide obtained by the heat decomposition of an iron halide and yellow iron oxide. Such a catalyst and the method of preparing such catalyst are disclosed is U.S. Patent Publication US2003/0144566, which publication is incorporated herein by reference. The catalyst taught in the publication may be used as the dehydrogenation catalyst of the inventive process; provided, that, it has the necessary low titanium content as noted elsewhere in this specification.

When red iron oxide and yellow iron oxide are mixed together in the preparation of the dehydrogenation catalyst of the inventive process, any suitable proportion of the two may be mixed together to form the mixture that is heat treated to give the finished dehydrogenation catalyst or the inventive process. Generally, however, the proportion of the yellow iron oxide used in the mixture is in the range of upwardly to about 50 weight percent, preferably, from 0 to 30 weight percent, of the total weight of the iron oxide in the mixture.

The promoter metal of the iron oxide based dehydrogenation catalyst of the inventive process may be selected from the group consisting of Sc, Y, La, Mo, W, Ce, Rb, Ca, Mg, V, Cr, Co, Ni, Mn, Cu, Zn, Cd, Al, Sn, Bi, rare earths and mixtures of any two or more thereof. Among the promoter metals, preferred are those selected from the group consisting of Ca, Mg, Mo, W, Ce, La, Cu, Cr, V and mixtures of two or more thereof. Most preferred, the promoter metal is selected from the group consisting of Ca, Mg, W, Mo, Ce and any combination of two or more thereof.

The portion of the iron oxide based dehydrogenation catalyst that is iron oxide is in the range of from 10 to 98 or even up to 100 weight percent with the weight percent being based on the total weight of the iron oxide based dehydrogenation catalyst and calculated as $Fe_2O_3$. It is preferred, however, for the iron oxide content to be in the range of from 40 to 90 weight percent, and, most preferred, from 60 to 85 weight percent.

The potassium (K) component may be present in the iron oxide based dehydrogenation catalyst in the range of from 5 to 40 weight percent with the weight percent being based on the total weight of the iron oxide based dehydrogenation catalyst and calculated as $K_2O$. Preferably, the potassium is present in the iron oxide based dehydrogenation catalyst in the range of from 5 to 35 weight percent, and, most preferably, from 10 to 30 weight percent.

Relative to the iron oxide ($Fe_2O_3$) contained in the finished iron oxide based dehydrogenation catalyst of the invention, the potassium component may be present therein in such an amount as to provide a ratio of the potassium component, calculated as K, to iron oxide that is in the range of from about 200 millimole (mmole) K per mole $Fe_2O_3$ to about 1600 mmole K per mole $Fe_2O_3$. Preferably, the potassium to iron oxide ratio is in the range of from 200 mmole K/mole $Fe_2O_3$ to 1400 mmole K/mole $Fe_2O_3$, and, most preferably, from 400 mmole K/mole $Fe_2O_3$ to 1200 mmole K/mole $Fe_2O_3$.

The alkaline earth metal component of the iron oxide based dehydrogenation catalyst can include either a magnesium (Mg) component or a calcium (Ca) component, or both components, and each such component alone or in combination may be present in the iron oxide based dehydrogenation catalyst in the range of from 0.1 to 15 weight percent with the weight percent being based on the total weight of the iron oxide based dehydrogenation catalyst and with the alkaline earth metal calculated as an oxide. Preferably, the alkaline earth metal is present in the iron oxide based dehydrogenation catalyst in the range of from 0.2 to 10 weight percent, and, most preferably, from 0.3 to 5 weight percent.

Relative to the iron oxide ($Fe_2O_3$) contained in the finished iron oxide based dehydrogenation catalyst of the invention, the alkaline earth metal component may be present therein in such an amount as to provide a ratio of the alkaline earth metal component, calculated as the element, to iron oxide that is in the range of from about 5 millimole (mmole) alkaline earth metal per mole $Fe_2O3$ to 750 mmole alkaline earth metal per mole $Fe_2O_3$. Preferably, the alkaline earth metal to iron oxide ratio is in the range of from 10 mmole alkaline earth metal/mole $Fe_2O_3$ to 500 mmole alkaline earth metal/mole $Fe_2O_3$, and, most preferably, from 15 mmole alkaline earth metal/mole $Fe_2O_3$ to 250 mmole alkaline earth metal/mole $Fe_2O_3$.

The cerium (Ce) component may be present in the iron oxide based dehydrogenation catalyst in the range of from 1 to 25 weight percent with the weight percent being based on the total weight of the iron oxide based dehydrogenation catalyst and calculated as $CeO_2$. Preferably, the cerium is present in the iron oxide based dehydrogenation catalyst in the range of from 2 to 20 weight percent, and, most preferably, from 3 to 15 weight percent.

Relative to the iron oxide ($Fe_2O_3$) contained in the finished iron oxide based dehydrogenation catalyst of the invention, the cerium component may be present therein in such an amount as to provide a ratio of the cerium component, calculated as Ce, to iron oxide that is in the range of from about 14 millimole (mmole) Ce per mole $Fe_2O_3$ to 350 mmole Ce per mole $Fe_2O_3$. Preferably, the cerium to iron oxide ratio is in the range of from 28 mmole Ce/mole $Fe_2O_3$ to 280 mmole Ce/mole $Fe_2O_3$, and, most preferably, from 42 mmole Ce/mole $Fe_2O_3$ to 200 mmole Ce/mole $Fe_2O_3$.

The molybdenum (Mo) component may be present in the iron oxide based dehydrogenation catalyst in the range of from 0.1 to 15 weight percent with the weight percent being based on the total weight of the iron oxide based dehydrogenation catalyst and calculated as $MoO_3$. Preferably, the molybdenum is present in the iron oxide based dehydrogenation catalyst in the range of from 0.2 to 10 weight percent, and, most preferably, from 0.3 to 5 weight percent.

Relative to the iron oxide ($Fe_2O_3$) contained in the finished iron oxide based dehydrogenation catalyst of the invention, the molybdenum or tungsten component may be present therein in such an amount as to provide a ratio of the molybdenum or tungsten component, calculated as Mo or W, to iron oxide that is in the range of from about 2 millimole (mmole) Mo or W per mole $Fe_2O_3$ to 300 mmole Mo or W per mole $Fe_2O_3$. Preferably, the molybdenum to iron oxide ratio is in the range of from 4 mmole Mo or W/mole $Fe_2O_3$ to 200 mmole Mo or W/mole $Fe_2O_3$, and, most preferably, from 6 mmole Mo or W/mole $Fe_2O_3$ to 100 mmole Mo or W/mole $Fe_2O_3$.

A preferred iron oxide based dehydrogenation catalyst composition of the invention has a low titanium concentration or an absence or substantial absence of titanium and comprises from 40 to 90 weight percent of the iron oxide component, as described herein, calculated as $Fe_2O_3$, and from 5 to 40 weight percent of a potassium component, calculated as $K_2O$. The iron oxide based dehydrogenation catalyst composition can further comprise from 1 to 25 weight percent of a cerium component, calculated as $CeO_2$; and, it further can comprise from 0.1 to 15 weight percent of a molybdenum component, calculated as $MoO_3$; and, it further can comprise from 0.1 to 15 weight percent an alkaline earth metal component, calculated as an oxide.

Another preferred iron oxide based dehydrogenation catalyst composition has a low titanium concentration or an absence or substantial absence of titanium and comprises from 40 to 90 weight percent of the iron oxide component, as described herein and calculated as $Fe_2O_3$, and a potassium component present in the iron oxide based dehydrogenation catalyst composition in such an amount as to provide a ratio of the potassium component, calculated as K, to iron oxide that is in the range of from about 200 millimole (mmole) K per mole $Fe_2O_3$ to about 1600 mmole K per mole $Fe_2O_3$. The iron oxide based dehydrogenation catalyst composition can further comprise a cerium component present in the iron oxide based dehydrogenation catalyst composition in such an amount as to provide a ratio of the cerium component, calculated as Ce, to iron oxide that is in the range of from about 14 millimole (mmole) Ce per mole $Fe_2O_3$ to 350 mmole Ce per mole $Fe_2O_3$; and it further can comprise a molybdenum component present in such an amount as to provide a ratio of the molybdenum component, calculated as Mo, to iron oxide that is in the range of from about 2 millimole (mmole) Mo per mole $Fe_2O_3$ to 300 mmole Mo per mole $Fe_2O_3$; and it further can comprise an alkaline earth metal component present in such an amount as to provide a ratio of the alkaline earth metal component, calculated as the element, to iron oxide that is in the range of from about 5 millimole (mmole) alkaline earth metal per mole $Fe_2O_3$ to 750 mmole alkaline earth metal per mole $Fe_2O_3$.

An especially preferred iron oxide based dehydrogenation catalyst comprises an iron oxide component, a cerium component, a potassium component, and an alkaline earth metal component, wherein all of such components are present in the iron oxide based dehydrogenation catalyst at any of the concentration ranges described above, and wherein the iron oxide based dehydrogenation catalyst contains titanium at a low titanium concentration as described in detail above. Another especially preferred iron oxide based dehydrogenation catalyst of the invention has a low titanium content and consists essentially of the iron oxide component, as described herein, a potassium component, a cerium component, a molybdenum or tungsten component, and an alkaline earth component.

The iron oxide based dehydrogenation catalyst of the invention is prepared by any method known to those skilled in the art. Generally, the catalyst is prepared by combining the catalyst components into a mixture, shaping the mixture to form particles, and then calcining the particles. The promoter metal-containing compounds may also be combined with the iron-containing and potassium-containing components.

The mixture of catalyst components can be formed into particles such as extrudates, pellets, tablets, spheres, pills, saddles, trilobes, tetralobes and the like. One preferred method of making the iron based dehydrogenation catalyst is to mix together the catalyst components with water or a plasticizer, or both, and forming an extrudable paste from which extrudates are formed. The extrudates are then dried and calcined. The calcination is preferably done in an oxidizing atmosphere, such as air, and at temperatures upwardly to 1200° C., but preferably from 500° C. to 1100° C., and, most preferably, from 700° C. to 1050° C.

The low titanium iron oxide based dehydrogenation catalysts of the invention are used in the dehydrogenation of dehydrogenatable hydrocarbons, and, further, they are used to improve the operation of existing dehydrogenation reactor systems that include a dehydrogenation reactor vessel in which is contained a dehydrogenation catalyst having a high titanium content that causes it to have unfavorable stability properties relative to the inventive catalysts by replacing such low stability dehydrogenation catalyst with the inventive catalyst. In the dehydrogenation method, the inventive catalyst is contacted with a dehydrogenation feed under dehydrogenation reaction conditions to thereby provide a dehydrogenation reaction product. More specifically, the dehydrogenation feed is introduced into the dehydrogenation reactor wherein it is contacted with the dehydrogenation catalyst bed under low steam-to-oil process conditions.

It is recognized that the dehydrogenation reactor or dehydrogenation reactor system can include more than one dehydrogenation reactor or reaction zone. If more than a single dehydrogenation reactor is used, they may be operated in series or in parallel, or they may be operated independently from each other or under the same or different process conditions.

The dehydrogenation feed can be any suitable feed and, more particularly, it can include any hydrocarbon that is dehydrogenatable. Examples of dehydrogenatable hydrocarbons include alkyl aromatics, such as alkyl substituted benzene and alkyl substituted naphthalene, isoamylenes, which can be dehydrogenated to isoprenes, and butenes, which can be dehydrogenated to butadiene. The preferred dehydrogenation feed comprises an alkylaromatic compound preferably one selected from the group of compounds consisting of ethylbenzene, propylbenzene, butylbenzene, hexylbenzene, methylpropylbenzene, methylethylbenzene, and diethylbenzene. The most preferred dehydrogenation feed is an ethylbenzene feedstock comprising predominantly ethylbenzene. Ethylbenzene is dehydrogenated to styrene. The dehydrogenation feed can also include other components including diluents. It is common to use steam as a feed diluent when ethylbenzene is a feed component to be dehydrogenated to form styrene.

The dehydrogenation conditions can include a dehydrogenation reactor inlet temperature in the range of from about 500° C. to about 1000° C., preferably, from 525° C. to 750° C., and, most preferably, from 550° C. to 700° C. It is recognized that in the dehydrogenation of ethylbenzene to styrene the reaction is endothermic. When such a dehydrogenation reaction is carried out, it can be done so either isothermally or adiabatically. In the case where the dehydrogenation reaction is carried out adiabatically, the temperature across the dehydrogenation catalyst bed, between the dehydrogenation reactor inlet and the dehydrogenation reactor outlet, can decrease by as much as 150° C., but, more typically, the temperature can decrease from 10° C. to 120° C.

The reaction pressure is relatively low and can range from vacuum pressure upwardly to about 200 kPa (29 psi). Typically, the reaction pressure is in the range of from 20 kPa (2.9 psia) to 200 kPa (29 psi). Due to the reaction kinetics of the dehydrogenation reaction of ethylbenzene to styrene it is generally preferable for the reaction pressure to be as low as is commercially feasible.

The liquid hourly space velocity (LHSV) can be in the range of from about 0.01 hr$^{-1}$ to about 10 hr$^{-1}$, and preferably, from 0.1 hr$^{-1}$ to 2 hr$^{-1}$. As used herein, the term "liquid hourly space velocity" is defined as the liquid volumetric flow rate of the dehydrogenation feed, for example, ethylbenzene, measured at normal conditions (i.e., 0° C. and 1 bar absolute), divided by the volume of the catalyst bed, or the total volume of catalyst beds if there are two or more catalyst beds.

The following Examples are presented to illustrate the invention, but they should not be construed as limiting the scope of the invention.

EXAMPLE I

This Example I describes the preparation of several iron oxide based dehydrogenation catalysts having varying concentrations of titanium. These catalysts were tested for their performance and stability as presented in Example II.

The iron oxide I used in the preparation of the catalysts below is a regenerator iron oxide prepared by roasting a waste pickle liquor solution containing $FeCl_2$. The resulting iron oxide ($Fe_2O_3$) had the composition and properties as presented in Table 1 below.

TABLE 1

| | |
|---|---|
| $SiO_2$ | 0.02-0.04 wt % |
| MnO | 0.40-0.50 wt % |
| $Al_2O_3$ | 0.06-0.07 wt % |
| $Cr_2O_3$ | 0.05-0.08 wt % |
| NiO | 0.03-0.04 wt % |
| Cl | 0.06-0.08 wt % |
| $TiO_2$ | 0.007-0.009 wt % |
| BET S.A. | 3.1-3.3 m$^2$/g |

The Iron Oxide II used in the preparation of the catalysts below was made by the same method as was used to prepare the Iron Oxide I; except, that, titanium was added during the preparation of the $Fe_2O_3$. The titanium was added as a titanium lactate salt (Dupont Tyzor® LA, containing 8.2% Ti) to the waste pickle liquor containing $FeCl_2$ and the mixture was roasted to produce the Iron Oxide II in the same manner as was the waste pickle liquor solution roasted in the preparation of the Iron Oxide I. The Iron Oxide II contained 0.053% $TiO_2$, but it otherwise had the same composition and properties as are presented in Table 1 above.

The Iron Oxide III was a yellow iron oxide, often called hydrated iron oxide or α-FeOOH. The calculated $Fe_2O_3$ content of the yellow iron oxide is 86% and the BET surface area was in the range of from 9.0-10.5 m$^2$/g. The titanium content of the Iron Oxide III was 0.004 wt % (40 ppmw).

Catalyst A was prepared first by forming a paste made by mixing the following ingredients: Iron Oxide I, Iron Oxide III, potassium carbonate, cerium carbonate, molybdenum trioxide, calcium carbonate, and water (about 8 wt. %, relative to the total weight of the dry mixture). The paste was then extruded to form 3-mm diameter cylinders that were cut into 6-mm lengths to form pellets. These pellets were then dried in air at 170° C. for 15 minutes and subsequently calcined in air at 825° C. for 1 hour. After calcination, the composition of Catalyst A nominally contained per mole of iron oxide, calculated as $Fe_2O_3$, about 0.516 mole potassium, 0.066 mole cerium, about 0.022 mole molybdenum, 0.027 mole calcium. When expressed in terms of the metal oxides, the finished catalyst contained 79.8% $Fe_2O_3$, 12.2% $K_2O$, 5.7% $CeO_2$, 1.6% $MoO_3$, and 0.5% CaO. The 80% $Fe_2O_3$ includes 72.6% $Fe_2O_3$ added as Iron Oxide I and 7.2% $Fe_2O_3$ added as Iron Oxide III. In addition to the added components, the catalyst contained about 30 ppm titanium.

Catalyst B was prepared in the same manner as Catalyst A, except that Iron Oxide II was used instead of Iron Oxide I. In addition to the components in Catalyst A, Catalyst B contained a total of about 250 ppm titanium.

Catalyst C was prepared in the same manner as Catalyst A, except that a different batch of Iron Oxide I was used. In addition to the component in Catalyst A, Catalyst C contained a total of about 40 ppm titanium.

Catalyst D was prepared in the same manner as Catalyst C, except that Tyzor® LA (DuPont titanium lactate solution containing 8.2% Ti) was added with the other catalyst ingredients. In addition to the components in Catalyst C, Catalyst D contained a total of about 250 ppm titanium.

Catalyst E was prepared in the same manner as Catalyst C, except that titanium oxide (TiO$_2$) was added with the other catalyst ingredients. In addition to the components in Catalyst C, Catalyst E contained a total of about 250 ppm titanium.

EXAMPLE II

This Example II describes the procedure for testing the performance of the catalysts described in Example I and presents the results of such testing.

Samples of Catalysts A through E were tested for their performance in the dehydrogenation manufacturing of styrene from ethylbenzene under isothermal testing conditions at a high steam-to-oil ratio in a reactor designed for continuous operation. A sample of each of the three catalyst samples was individually tested under the following testing conditions: absolute pressure 76 kPa, steam-to-ethylbenzene molar ratio 10, LHSV 0.65 l/l.h. In each test run, the reactor temperature was set at 600° C. for the first 7 to 10 days as the catalyst was activated and broken in. Thereafter, the reactor temperature was adjusted daily such that in each test run a 70% mole conversion of ethylbenzene was achieved.

FIG. 1 presents plots comparing the activity as reflected by the T(70) temperature for each of the catalysts when the catalysts were used under high steam-to-oil process conditions as a function of the time in use. It may be observed from the plots that Catalysts A and C containing the low titanium concentration exhibited a lower initial activity, i.e., higher T(70) temperature, than the activity exhibited by the Catalysts B, D, and E that contained the higher titanium concentration. However, after about 10 days Catalysts A and C showed stable performance and higher activity than Catalysts B, D, and E, which continued to exhibit activity decline.

After the period of time as indicated in FIG. 1, the reaction conditions were changed by reducing the pressure from 76 kPa to 40 kPa and reducing the steam to ethylbenzene ratio from 10 to 5 molar. After the first 4 days at these conditions the reactor temperatures were adjusted such that in each test run a 70% mole conversion of ethylbenzene was achieved. FIG. 2 shows that Catalysts A and C exhibit improved activity after equilibration as compared to Catalysts B, D, and E, which continue to exhibit a decline in performance and inoperability.

FIG. 3 presents plots comparing the selectivity as reflected by the S(70) selectivity value for each of the catalysts when the catalysts were used under high steam-to-oil process conditions as a function of the time in use. As may be observed from the plots, the catalysts containing the low titanium concentration exhibited equivalent or reduced selectivity, i.e., lower S(70) selectivity value, than the selectivity exhibited by the catalysts containing the higher titanium concentration.

By contrast, the plots presented in FIG. 4 compare the selectivity of the catalysts used under low steam-to-oil process conditions as a function of time in use. The data presented show that, unexpectedly, the relative selectivities of the catalysts are reversed as compared to their relative selectivities when the catalysts are used under high steam-to-oil process conditions. When used under low steam-to-oil conditions, the catalysts containing the low concentration of titanium actually exhibit a higher selectivity than the catalysts containing the higher concentration of titanium.

The data presented in the figures demonstrate that the iron oxide based catalyst having the higher concentration of titanium may exhibit better initial activity and selectivity than those exhibited by the iron oxide based catalyst having a lower titanium concentration when the catalysts are used under high steam-to-oil process conditions. But, on the otherhand, the data also demonstrate that the catalysts with the lower titanium concentrations perform substantially better than the catalysts with the higher titanium concentrations when the catalysts are used under low steam-to-oil process conditions. In particular, the low titanium catalysts show improved activity under low steam-to-oil process conditions and more stable operation with less activity decline. These unique properties demonstrate that the low titanium content iron oxide based dehydrogenation catalysts, when used in a dehydrogenation process operated under low steam-to-oil process conditions, may be exploited to provide the inventive improved dehydrogenation process or otherwise to provide an improved operation of a dehydrogenation process.

The improved operation of the dehydrogenation process results not only from the use of a catalyst that has the desirable properties of high activity and selectivity, but, also, from the operation of a dehydrogenation process under low steam-to-oil process conditions. The ability to acceptably operate a dehydrogenation process at low steam-to-oil process conditions provides many benefits including those mentioned above.

Reasonable variations, modifications and adaptations of the invention may be made within the scope of the described disclosure and appended claims without departing from the spirit and scope of the invention.

That which is claimed is:

1. In a process for manufacturing styrene, which said process is of the type wherein an ethylbenzene feed is contacted under dehydrogenation conditions with a catalyst to yield a styrene product, the improvement comprises:
   utilizing as said catalyst an iron oxide based dehydrogenation catalyst composition having a titanium content from about 30 ppmw to less than 100 ppmw; and
   operating said process under a steam-to-oil ratio operating condition, wherein the molar steam-to-oil ratio is no more than 9:1.

2. A process as recited in claim 1, wherein said titanium concentration is less than 75 ppmw, and wherein said molar steam-to-oil ratio is less than 8:1.

3. A dehydrogenation process, comprising:
   contacting under dehydrogenation conditions a feed with an iron oxide based dehydrogenation catalyst having a titanium content from about 30 ppmw to less than 100 ppmw wherein said feed comprises ethylbenzene and steam, and wherein said steam is present in said feed in an amount so as to provide a molar steam-to-oil ratio in said feed of less than 9:1.

4. A dehydrogenation process as recited in claim 3, wherein said molar steam-to-oil ratio is less than 8:1, and wherein said titanium concentration is less than 75 ppmw.

* * * * *